United States Patent [19]
Wang et al.

[11] Patent Number: 5,316,855
[45] Date of Patent: * May 31, 1994

[54] HIGH ABRASION RESISTANCE COATING MATERIALS FROM ORGANIC/INORGANIC HYBRID MATERIALS PRODUCED BY THE SOL-GEL METHOD

[75] Inventors: Bing Wang; Garth L. Wilkes, both of Blacksburg, Va.

[73] Assignee: Virginia Tech Intellectual Properties, Inc., Blacksburg, Va.

[*] Notice: The portion of the term of this patent subsequent to Nov. 19, 2007 has been disclaimed.

[21] Appl. No.: 615,569

[22] Filed: Nov. 19, 1990

Related U.S. Application Data

[63] Continuation-in-part of Ser. No. 552,632, Jul. 13, 1990, abandoned.

[51] Int. Cl.$^5$ .............................................. B32B 9/04
[52] U.S. Cl. ............................. 428/447; 106/287.12; 106/287.16; 428/412; 428/469; 525/105
[58] Field of Search ....................... 428/412, 447, 469; 106/287.12, 287.16; 525/105

[56] References Cited

U.S. PATENT DOCUMENTS 4,719,262  1/1988  Plueddemann ................... 525/105
4,746,366  5/1988  Philipp et al. ..................... 428/412

Primary Examiner—Paul J. Thibodeau
Assistant Examiner—Hoa T. Le
Attorney, Agent, or Firm—Richard P. Fennelly; Louis A. Morris

[57] ABSTRACT

A series of new high abrasion resistance coating materials have been prepared utilizing organic/inorganic hybrid materials formed by cohydrolyzing a metal alkoxide sol (e.g. silicon, aluminum, titanium, or zirconium metal alkoxide sol) with one or more bis(trialkoxysilane-containing) organic components or related functionalized species. These hybrid materials show optical clarity and improve the abrasion resistance of polymer substrates when applied as coatings and cured on such substrates.

6 Claims, 4 Drawing Sheets

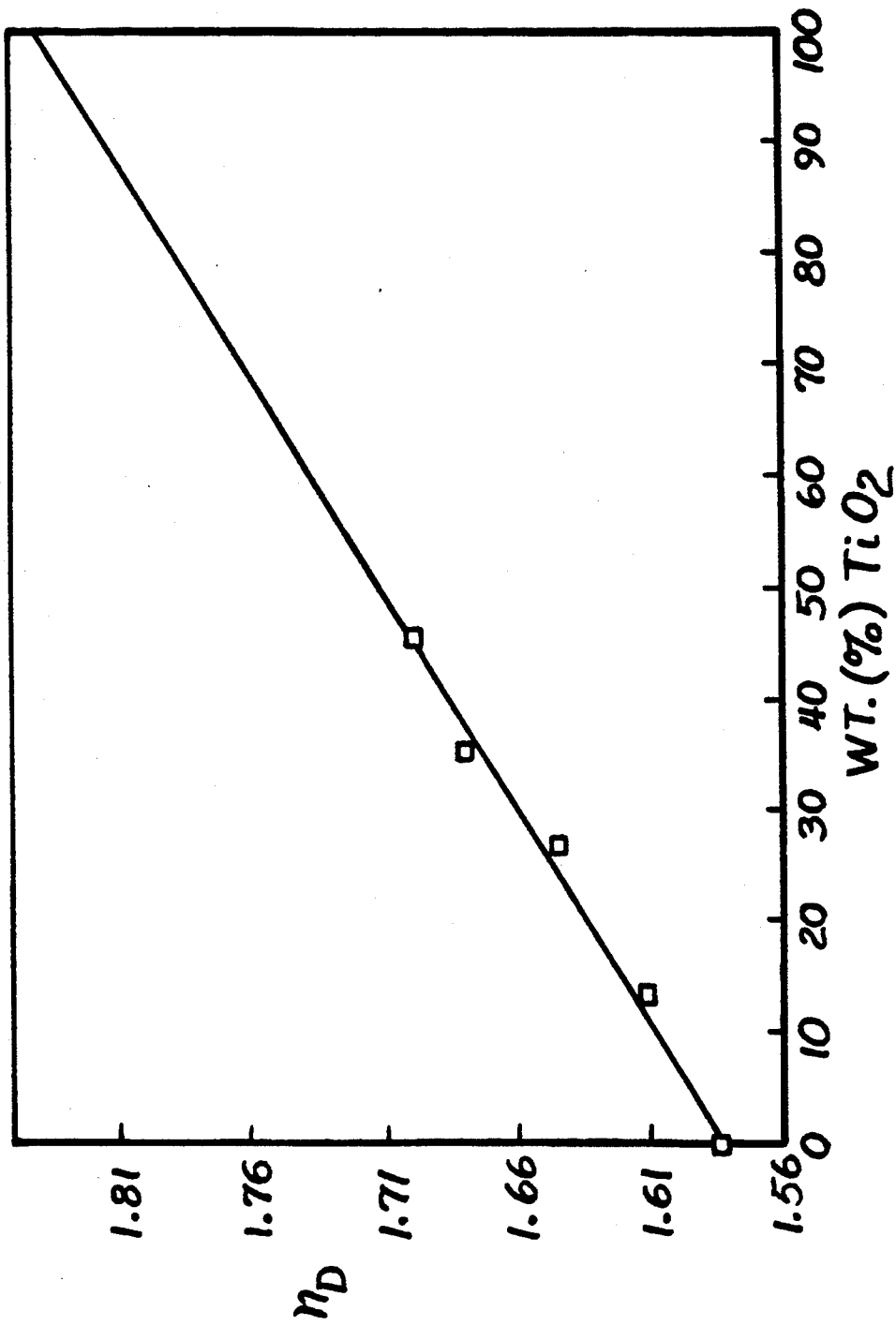

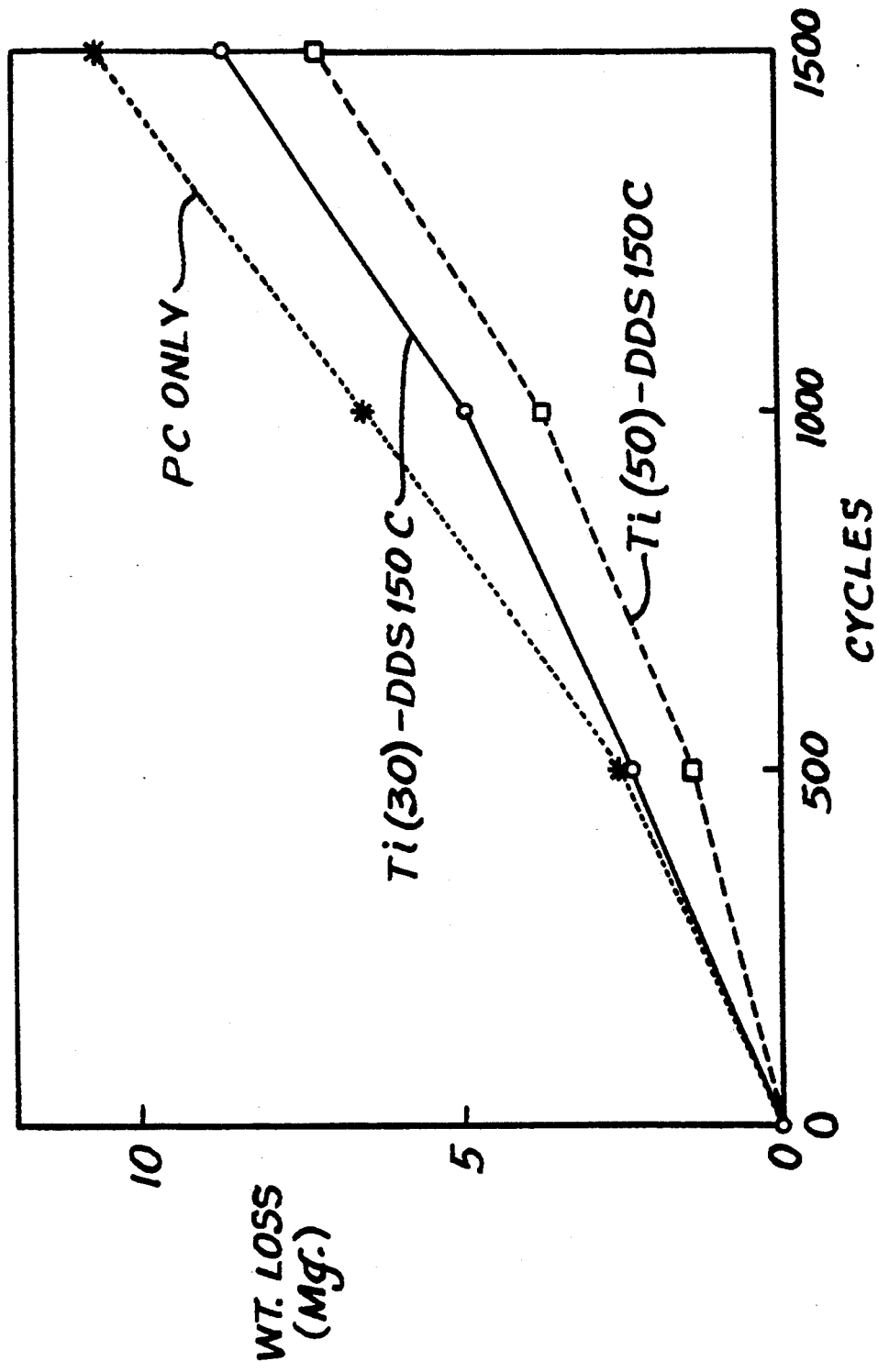

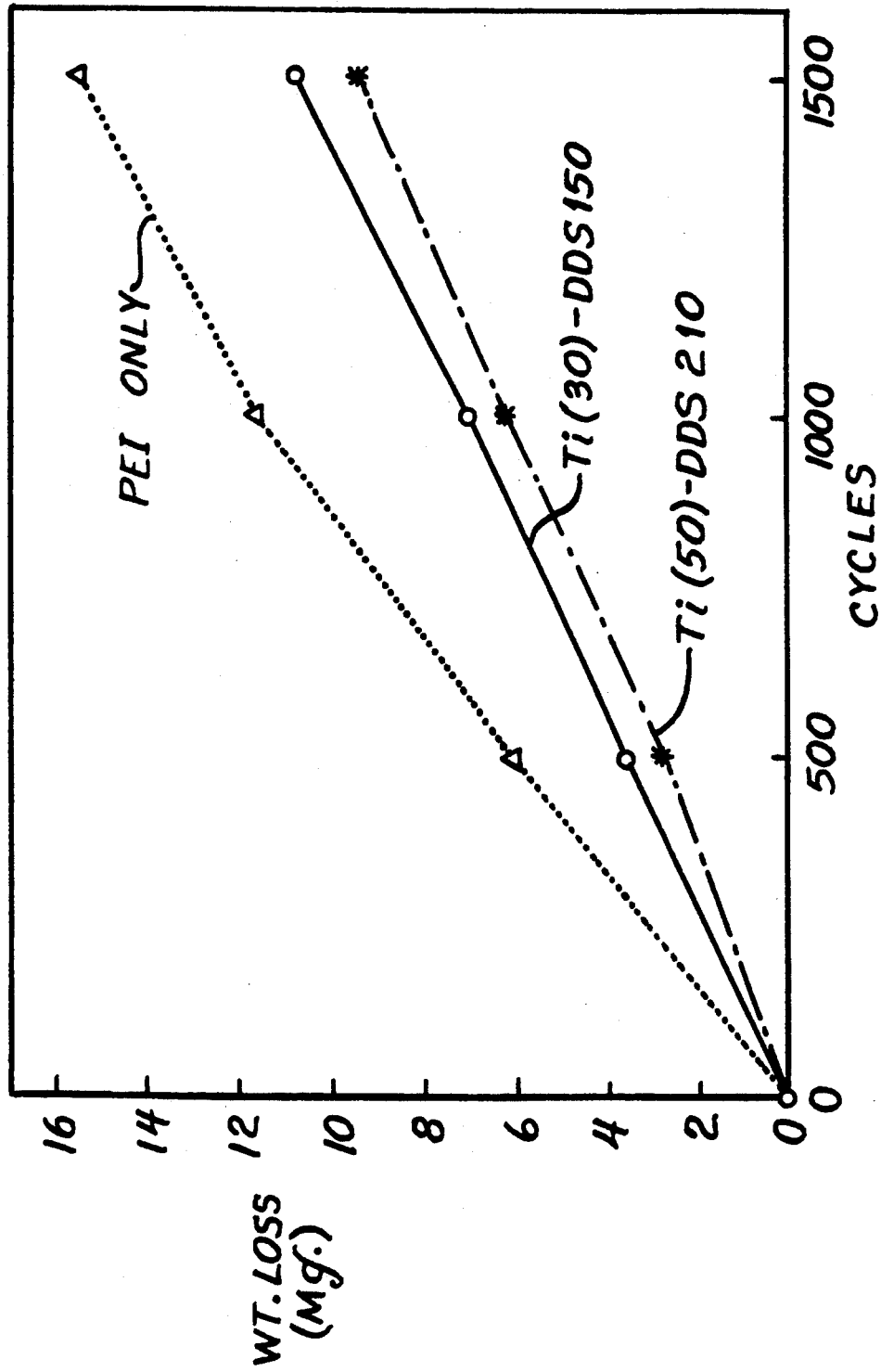

HIGH ABRASION RESISTANCE COATING MATERIALS FROM ORGANIC/INORGANIC HYBRID MATERIALS PRODUCED BY THE SOL-GEL METHOD

This is a continuation-in-part of U.S. Ser. No. 552,632, filed Jul. 13, 1990, now abandoned.

BACKGROUND OF INVENTION

Various types of protective coating materials have been used to improve the abrasion resistance and hardness of polymer surfaces( e.g., polycarbonate resin). For example, Ishigaki et al. improved the scratch resistance of polymethylmethacrylate (PMMA) by utilizing silane compounds as coating materials (Jpn. Kokai Tokkyo Koho JP 63 48,364). Komatsu et al. used a mixed inorganic composition of zirconate-silicate with a $SnO_2$ sol as an antistatic and scratch resistance coating material (Jpn. Kokai Tokkyo Koho JP 63,152,675). Nishiuchi et al. also obtained an abrasion resistant and glossy coating material from a mixed system of alkali metal oxides (Jpn. Kokai Tokkyo Koho JP 63,992268). Yamada et al. used zirconium-containing organosiloxanes as hard coating materials which were based on a 1:1 molar ratio of $Zr(OBu)_4$ with $Si(MeO)_3H$ and ethylacetoacetate as the chelating agent (Jpn. Kokai Tokkyo Koho JP 64 01,769 [89 01,769]). A pencil hardness value 4H was observed for the Yamada et al. system. Based on the same composition without $Zr(OBu)_4$, the pencil hardness value was reduced to only an HB value. The disclosure of these references describe coatings, which provide good adhesion of coatings on polymer, but which are limited to inorganic systems with no organic component.

U.S. Pat. No. 4,929,278 also discloses various sol-gel derived coatings on plastics which are also inorganic in nature and do not contain organic moieties.

U.S. Pat. No. 4,746,366 to G. Philipp et al. describes the formation of scratch-resistant coatings, which can be applied to plastic substrates, which are formed by the hydrolytic polycondensation of at least one titanium or zirconium compound (such as tetraethyl titanate or tetrapropyl zirconate) and at least one organofunctional silane. In these systems, the organic moiety has a single silane functionality at one end which is capable of hydrolytic polycondensation with the titanium or zirconium compound.

DESCRIPTION OF THE DRAWINGS

The Drawings form a portion of the instant specification wherein:

FIG. 2 shows the refractive index of the Ti-DDS hybrid materials versus the $TiO_2$ content for various samples. The various $TiO_2$ weight percent values were obtained, in ascending order, from use of 30 wt %, 50 wt %, 60 wt % and 70 wt % titanium tetraisopropoxide based on the total weight of the reactive components;

FIG. 3 shows the Taber abrasion test data using a CS-10 ASTM wheel for a titanium-containing triethoxysilane-capped 4,4'-diaminophenyl sulfone (Ti-DDS) coating on bisphenol-A polycarbonate. The designation "Ti(30)-DDS150C" represents 30% of titanium tetraisopropoxide relative to the total weight of DDS and titanium isopropoxide with the final curing temperature being 150° C. Ti(50)-DDS150C is the same as Ti(30)-DDS150C except that 50 wt % of titanium tetraisopropoxide was utilized; and FIG. 4 illustrates Taber abrasion test data using a CS-10 ASTM wheel for Ti-DDS on poly(ether imide), called "PEI", with the sample designation in the Figure following that given in FIG. 3.

DESCRIPTION OF INVENTION

Figure 1:
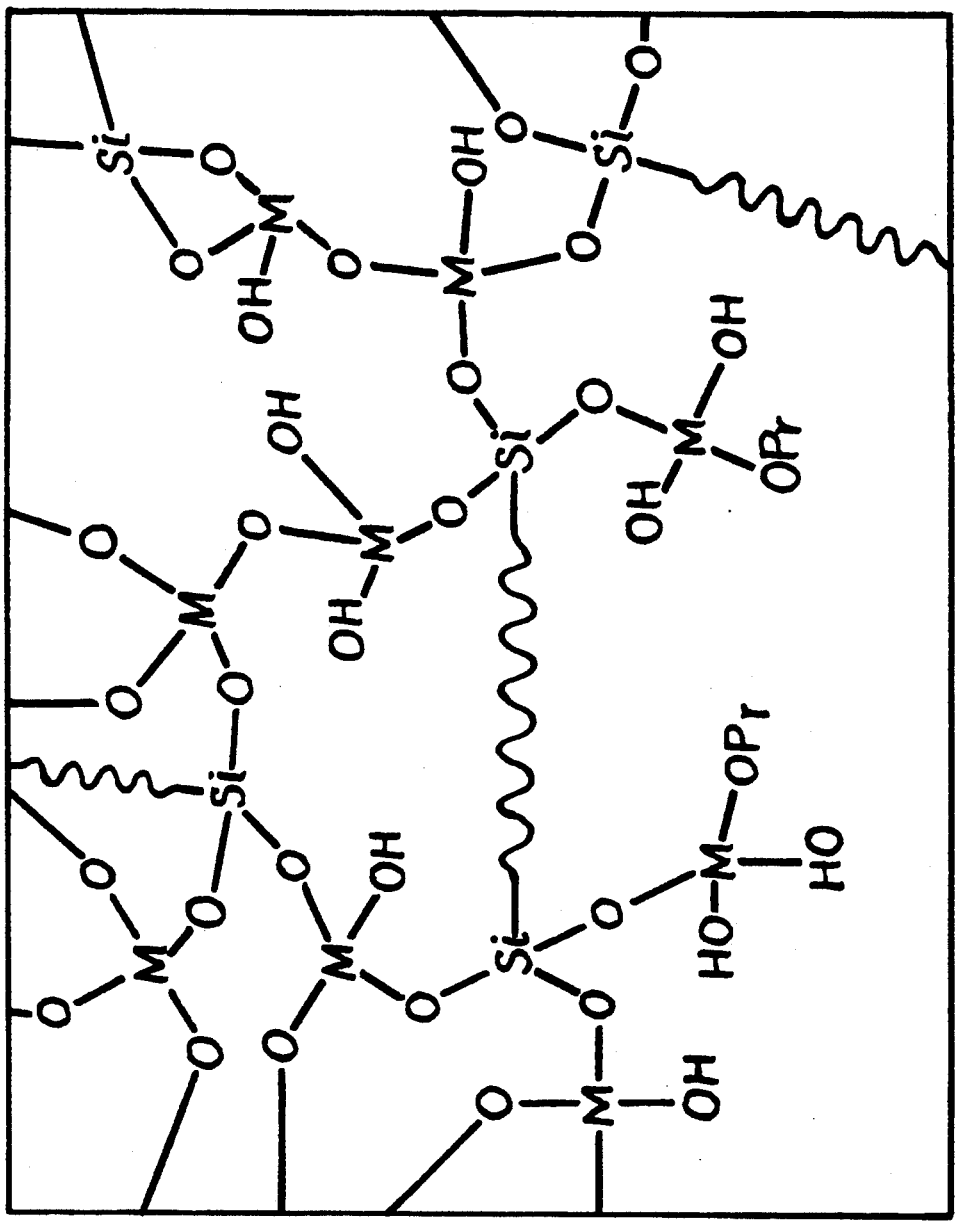
FIG. 1 is a schematic which depicts a suggested general network model for the hybrid network organic/inorganic hybrids or "ceramers" used as coatings herein.

A series of new high abrasion resistance coating hybrid materials have been developed by cohydrolyzing a metal alkoxide sol (e.g., a silicon, aluminum, titanium, or zirconium metal alkoxide sol or mixtures thereof) with at least one trialkoxysilane-containing organic component having the trialkoxysilane. The basic cohydrolysis reaction in which the selected metal alkoxide or alkoxides is reacted with the trialkoxysilane-containing organic component or related functionalized (i.e., trialkoxy-capped) material is well known in the art to persons familiar with sol-gel chemistry. The terminology "trialkoxysilane-containing organic component" is intended to cover, for example, the bis-tri(lower)alkoxysilane-containing materials (e.g., those containing triethoxysilane) which are alkoxysilane end-capped at more than one location and which are capable of sol-gel reaction with the aforementioned types of metal reactants. Generally speaking, the amount of metal alkoxide to combined amount of metal alkoxide and trialkoxysilane-containing organic component will range from about 5% to about 95%, by weight.

The trialkoxy-capped organic material can include an organo-portion which is less rigid (as in the case of 1,6-bis(trimethoxysilyl) hexane) or which is of a more rigid aromatic nature (as in the case of triethoxysilane-capped bis(3-aminophenoxy-4'-phenyl) phosphine oxide or a 4,4'-diaminophenyl sulfone with triethoxysilane end capping. Another class of material are alkoxysilane-capped polyalkylenepolyamine compounds.

The hybrid materials used as coatings herein show good optical clarity and improve the abrasion resistance of polymer substrates after the substrate has been coated with the hybrid material and the coating is cured.

If desired, the polymer can be pretreated with a plasma to improve the adhesion of the organic/inorganic hybrid coating thereon. Further details in regard to such a plasma pretreatment can be found in copending U.S. Ser. No. 615,568, filed on even date herewith, entitled "Plasma Improved Adhesion of Coatings Comprising Metal Oxide Ceramics On Polymeric Substrates", which is incorporated herein by reference.

The instant invention is further illustrated by the Examples which follow.

EXAMPLE 1

This Example shows preparation of triethoxysilane-capped 4,4'-diaminophenyl sulfone(DDS) having the general formula:

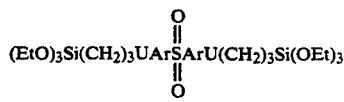

where Et is ethyl, U is —NHC(O)NH— and Ar is phenylene.

First, 17.78 g of 4,4'-diaminophenyl sulfone (DDS) was dissolved into 40.5 g of N,N-dimethylformamide (DMF). Next, 43.5 g of 3-isocyanatopropyl-triethoxysilane was slowly added to this solution and was stirred for three hours. The solution was kept under nitrogen before using.

EXAMPLE 2

This Example shows preparation of triethoxysilane-capped bis(3-aminophenoxy-4'-phenyl) phosphine oxide(BAPPO) having the general formula:

where Et, U, and Ar have the meaning given above.

First, 2.83 g of bis(3-aminophenoxy-4'-phenyl)phosphine oxide (BAPPO) was dissolved in 6.5 g of DMF. Next, 3.5 g of 3-isocyanatopropyl-triethoxysilane was slowly added to this solution and was stirred for three hours. The solution was kept under nitrogen before using.

It is deemed that coatings containing BAPPO will have some enhanced degree of fire retardancy due to the phosphorus atom in such a compound.

EXAMPLE 3

This Example illustrates preparation of a Ti-DDS sol for use as a coating on a polymer.

First, 0.6 ml of deionized water, 0.1 ml of HCl (10N), and 5 g of isopropanol were mixed together in a flask and then transferred to an addition funnel. Next, the HCl-containing isopropanol was slowly added to a polypropylene flask which contained 5 g of titanium isopropoxide. In order to avoid local inhomogeneity, it was crucial to maintain a slow addition rate of the HCl-containing isopropanol solution and to utilize a fast stirring rate. This procedure developed a clear titania sol (pH=2.2). Then, a solution containing an appropriate amount of triethoxysilane-capped DDS was mixed with the titania sol and was stirred for 27 hours to obtain a viscous homogeneous system for coating on polymeric surfaces (e.g., polycarbonate, polyimide, etc.). The coating was then cured by thermal heating to 150° C. at about 1°-2° C. per minute. The temperature of 150° C. was held for 5-10 minutes and then the sample was slowly cooled to about 70° C. after which the material was removed from the oven and later tested.

EXAMPLE 4

This Example illustrates preparation of a Zr-BAPPO sol for use as a coating on a polymer First, 0.1 ml of HCl (10N), and 5 g of isopropanol were mixed together in a flask. Then the solution was transferred to an addition funnel. Next, the HCl-containing isopropanol was slowly added to a polypropylene flask which contained 5 g of zirconium tetraisopropoxide. In order to avoid local inhomogeneity, it was crucial to maintain a slow addition rate of the HCl-containing isopropanol solution and to utilize a fast stirring rate. This procedure developed a clear zirconia sol (pH=2.2). Then a solution containing an appropriate amount of triethoxysilane-capped BAPPO (Example 2) was mixed with the zirconia sol and stirred for 27 hours to obtain a viscous homogeneous system for coating on polymeric surfaces (e.g. polycarbonate, polyimide etc.) by either a dip or spin coating procedure. After drying in an oven at 60° C. for four hours, these coated samples were annealed (cured) at a minimum of 120° C. before testing. The procedure for curing was similar to that given in Example 3.

EXAMPLE 5

This Example illustrates preparation of a triethoxysilane-capped diethylenetriamine (DETA) for use in Example 6.

First, 5 g of DETA was mixed with 20 g of isopropanol. Then 40 g of 3-isocyanatopropyltriethyoxysilane was slowly added to this solution and was stirred for three hours to yield the desired product which was of the formula:

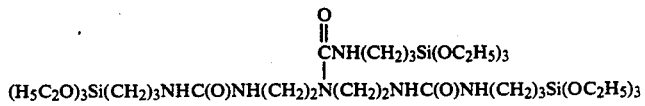

EXAMPLE 6

This Example illustrates preparation of a Ti-DETA sol for coatings.

First, 0.1 ml of HCl (10N), 0.6 ml of H$_2$O, and 5 g of isopropanol were mixed together in a flask. Then the alcohol solution was transferred to an addition funnel. Next, the HCl-containing isopropanol was slowly added to a polypropylene flask which contained 5 g of titanium tetraisopropoxide. In order to avoid local inhomogeneity, it was crucial to maintain a slow addition rate of the HCl-containing isopropanol solution and to utilize a fast stirring rate. This procedure developed a clear titania sol (pH=2.2). Then a solution containing an appropriate amount of triethoxysilane-capped DETA was mixed with the titanium sol and stirred for 27 hours to obtain a viscous homogeneous system for coating on polymeric surfaces (e.g. polycarbonate, polyimide etc.) by either a dip or spin coating procedure. After drying in an oven at 60° C. for four hours, these coated samples were annealed (cured) at a minimum of 120° C. using a curing similar manner as utilized in Examples 3 and 4.

EXAMPLE 7

This Example illustrates preparation of a Zr-DETA sol for coatings.

First, 0.1 ml of HCl (10N), and 5 g of isopropanol were mixed together in a flask. Then the solution was transferred to an addition funnel. Next, the HCl-containing isopropanol was slowly added to a polypropylene flask which contained 5 g of zirconium tetraisopropoxide. In order to avoid local inhomogeneity, it was crucial to maintain a slow addition rate of the HCl-containing isopropanol solution and to utilize a fast stirring rate. This procedure developed a clear zirconia sol (pH=2.2). Then a solution containing an appropriate amount of triethoxysilane-capped DETA was mixed with the zirconium sol and stirred for 27 hours to obtain a viscous homogeneous system for coatings on polymeric surfaces (e.g. polycarbonate, polyimide etc.) by either a dip or spin coating procedure. After drying in an an oven at 60° C. for four hours, these coated samples were annealed (cured) at a minimum of 120° C. before testing. The curing procedure was similar to that utilized in Examples 3, 4 and 6.

EXAMPLE 8

This Example illustrates the results of a visible light measure transmission test on the wear area of a coated polymer sample that had undergone a Taber abrasion test at a load of 250 g using ASTM Taber wheel CS10. The light beam was 0.4×10 mm and the wavelength was 420 nm.

The samples tested were:
- A=50% titanium tetraisopropoxide relative to the amount of the BAPPO component and the titanium alkoxide component on bisphenol A polycarbonate with a curing temperature of 145° C.
- B=same as A with the exception that a 30% level of the titanium isopropoxide was used.
- C=same as A with the exception that a 50% level of zirconium isopropoxide was used.
- D=polycarbonate with no coating at 150° C. cure.

The results are as follows with higher percentages being indicative of less wear.

| Wheel Cycles | Percentage Transmission of Sample | | | |
|---|---|---|---|---|
| | A | B | C | D |
| 0 | 100 | 100 | 100 | 100 |
| 10 | 98.0 | 98.3 | 98.6 | 94.3 |
| 50 | 96.6 | 96.8 | 97.1 | 91.8 |
| 200 | 94.1 | 94.1 | 94.5 | 89.7 |

EXAMPLE 9

The test used in Example 8 was carried out with various metal-DETA coatings. The samples were:
- A=50 wt % zirconium isopropoxide relative to the amount of the DETA component and zirconium alkoxide component, and cured at 145° C.
- B=same as A with 30% zirconium isopropoxide being used.
- C=same as A with titanium isopropoxide being substituted.
- D=polycarbonate with no coating at 150° C. cure.

The results were:

| Wheel Cycles | Percentage Transmission of Sample | | | |
|---|---|---|---|---|
| | A | B | C | D |
| 0 | 100 | 100 | 100 | 100 |
| 10 | 99.2 | 98.7 | 99.1 | 94.3 |
| 50 | 98.3 | 98.2 | 98.2 | 91.8 |
| 200 | 97.6 | 97.3 | 96.4 | 89.7 |

EXAMPLE 10

A sheet of isotactic poly (4-methyl-1-pentene), termed "PMP", which was 3.5 by 3.5 inches square and 1/16 inch in thickness was wiped with ethanol soaked KIMWIPE fabric. The sheets were then dried with the same dry fabric to insure that the surface was dry. Next, this sample was placed in a plasma chamber and pumping was commenced to reach a vacuum of less than 2 torr. Before turning on the plasma, the gas line was flushed for five minutes with oxygen. Then, the plasma source was turned on for five minutes. Following the plasma treatment, the polymer substrate was coated with a zirconium-containing organic/inorganic based sol which also contained moieties derived from the triethoxysilane-functionalized diethylenetriamine. Example 7 illustrates formation of such a Zr-DETA sol.

The following results were obtained in regard to abrasion resistance using the type of test described in Examples 8 and 9 for a 30 wt % zirconium isopropoxide-70% functionalized DETA-derived coating which was cured at 145° C. on PMP:

| Wheel Cycles | PMP Alone | PMP with Cured Coating |
|---|---|---|
| 10 | 76.1 ± 3.3 | 98.3 ± 0.3 |
| 50 | 67.6 ± 2.5 | 96.3 ± 0.5 |

The foregoing Examples illustrate certain embodiments of the instant invention and should not, for that reason, be construed in a limiting sense. The scope of protection sought is set forth in the claims which follow.

We claim:

1. A coated polymer which comprises a polymer substrate and a coating of a cured organic/inorganic hybrid material formed by the sol-gel cohydrolyzation of a metal alkoxide and a trialkoxysilane-containing organic component which contains trialkoxysilane groups at more than one location.

2. A coated polymer as claimed in claim 1 wherein the trialkoxysilane-containing material is a bis-triethoxysilane-containing material.

3. A coated polymer as claimed in claim 1 wherein the metal alkoxide is selected from the group consisting of silicon, aluminum, titanium and zirconium.

4. A coated polymer as claimed in claim 2 wherein the metal alkoxide is selected from the group consisting of silicon, aluminum, titanium and zirconium.

5. A coated polymer as claimed in claim 1 wherein the relative amount of metal alkoxide to the combined amount of metal alkoxide and trialkoxysilane-containing organic component is from about 5% to about 95%, by weight.

6. A coated polymer as claimed in claim 4 wherein the amount of metal alkoxide to the combined amount of metal alkoxide and trialkoxysilane-containing organic component is from about 5% to about 95%, by weight.

* * * * *